United States Patent
Lafontaine

(10) Patent No.: US 6,929,639 B2
(45) Date of Patent: Aug. 16, 2005

(54) CRYO ABLATION COIL

(75) Inventor: Daniel M. Lafontaine, Plymouth, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 198 days.

(21) Appl. No.: 10/231,738

(22) Filed: Aug. 30, 2002

(65) Prior Publication Data

US 2004/0044334 A1 Mar. 4, 2004

(51) Int. Cl.[7] .............................................. A61B 18/18
(52) U.S. Cl. ............................ 606/20; 606/21; 606/22; 606/23; 606/25
(58) Field of Search .............................. 606/20, 21, 22, 606/23, 24, 25, 26; 607/96, 104, 105, 113

(56) References Cited

U.S. PATENT DOCUMENTS

| | | |
|---|---|---|
| 4,278,090 A | 7/1981 | van Gerven |
| 5,147,355 A | 9/1992 | Friedman et al. |
| 5,281,215 A | 1/1994 | Milder |
| 5,334,193 A | 8/1994 | Nardella |
| 5,624,392 A | 4/1997 | Saab |
| 5,807,391 A | 9/1998 | Wijkamp |
| 6,024,740 A | 2/2000 | Lesh et al. |
| 6,290,696 B1 | 9/2001 | Lafontaine |
| 6,355,029 B1 | 3/2002 | Joye et al. |
| 2001/0037081 A1 | 11/2001 | Heiner |
| 2002/0022832 A1 * | 2/2002 | Mikus et al. ................. 606/20 |
| 2002/0032438 A1 | 3/2002 | Lafontaine |
| 2002/0045892 A1 | 4/2002 | Kramer |
| 2002/0091378 A1 | 7/2002 | Dobak, III et al. |

FOREIGN PATENT DOCUMENTS

| | | |
|---|---|---|
| GB | 2 283 678 | 5/1995 |
| WO | WO 02/07625 | 1/2002 |

* cited by examiner

*Primary Examiner*—Rosiland Rollins
(74) *Attorney, Agent, or Firm*—Fish & Richardson P.C., P.A.

(57) ABSTRACT

The present invention pertains to devices for causing cold-induced necrosis or apoptosis. The present invention includes a cryo therapy apparatus including a core member; a cryoplasty tube coupled to the core member, the cryoplasty tube having a proximal end and a distal end; wherein the distal end includes a coil disposed about at least a portion of the tubular sheath, the coil including at least one opening; an outer tube disposed over at least a portion of the cryoplasty tube; and a cooling member disposed over the coil and coupled to the outer tube. A method of causing cold-induced necrosis is also disclosed.

39 Claims, 6 Drawing Sheets

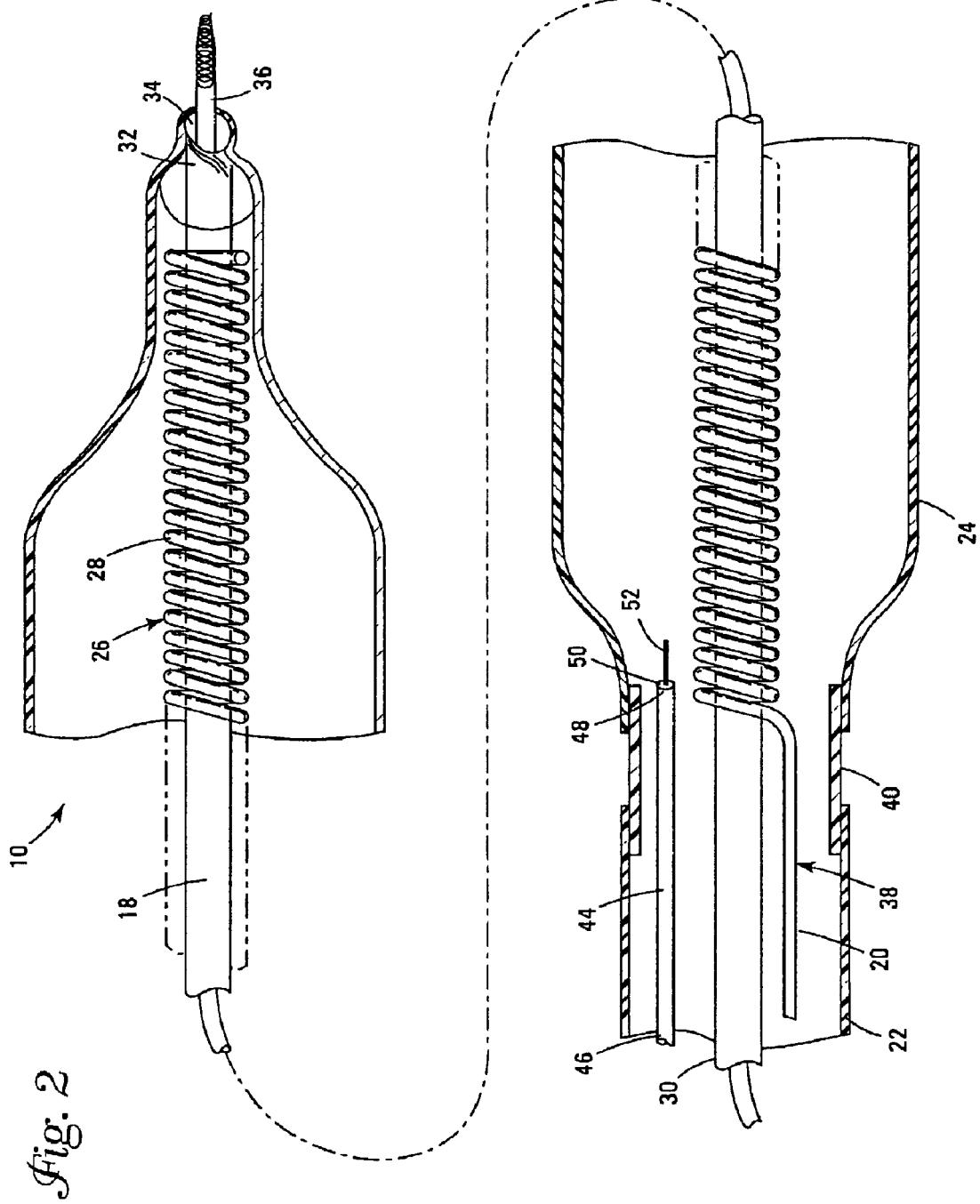

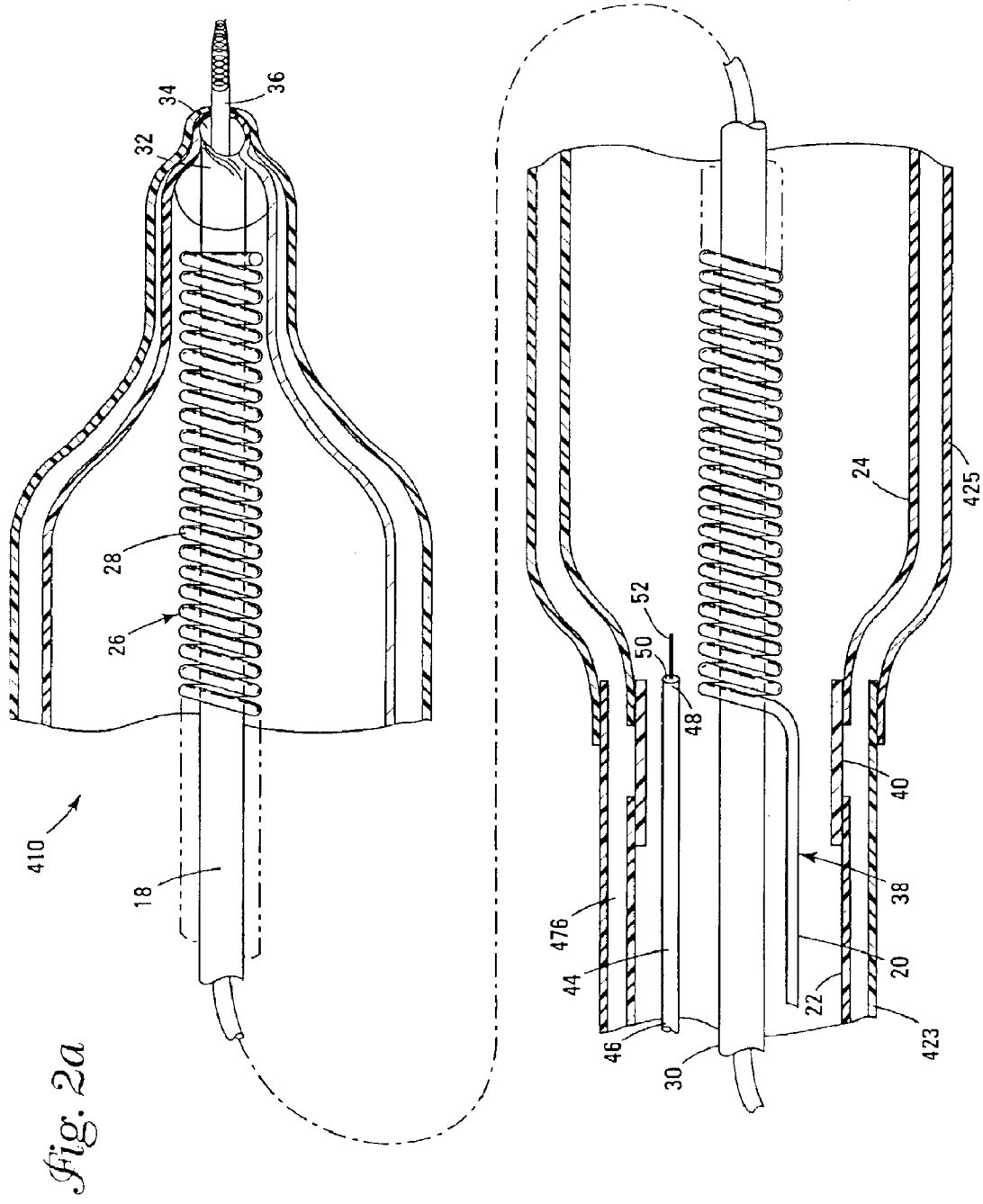

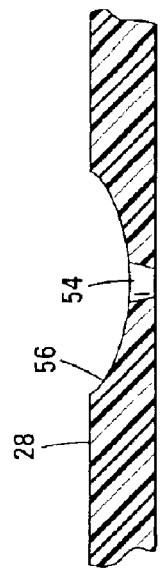
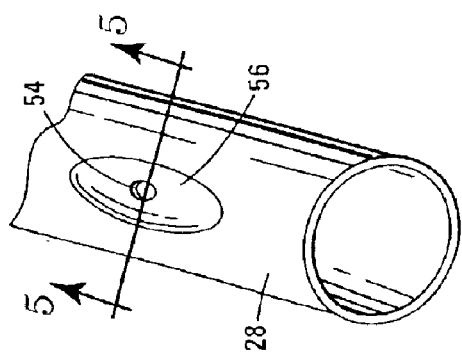
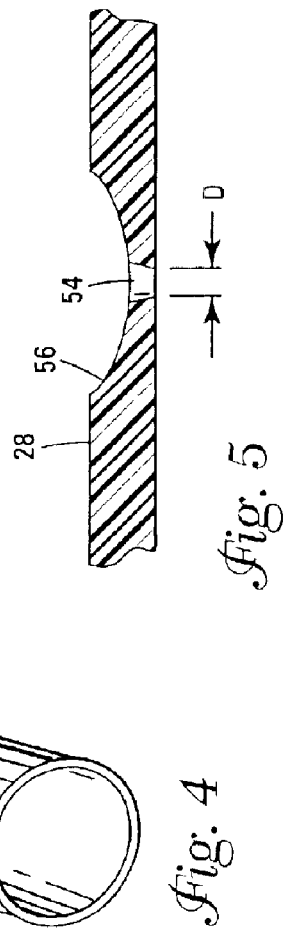
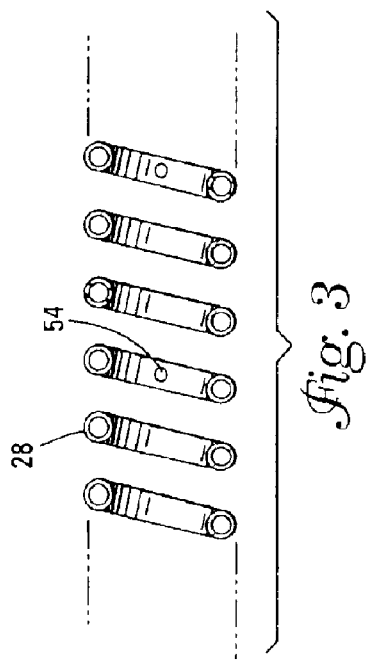
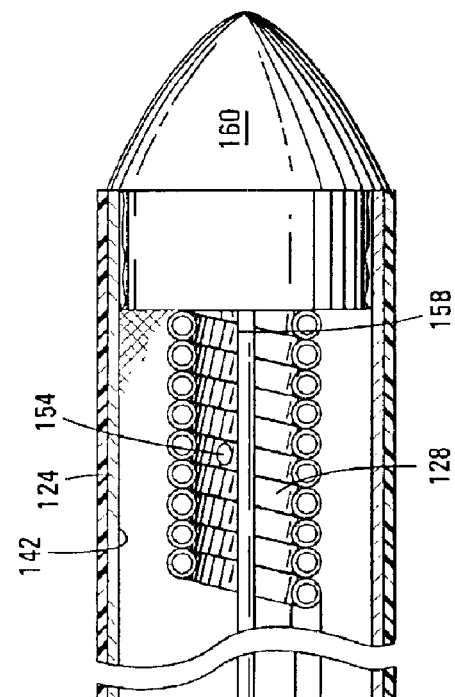
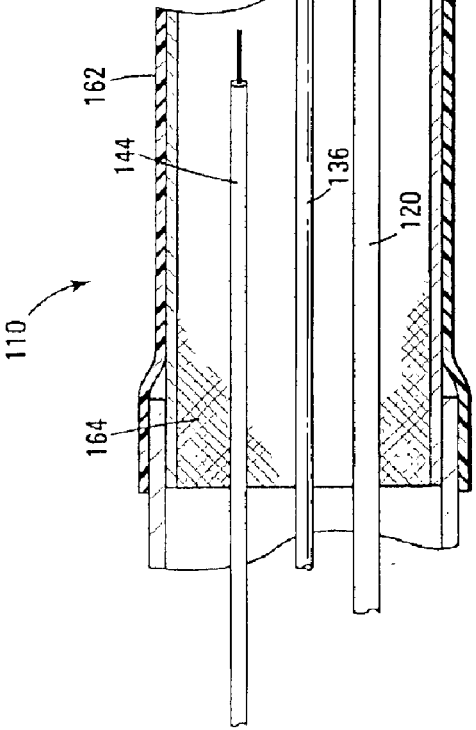

CRYO ABLATION COIL

FIELD OF THE INVENTION

The present invention pertains generally to the field of cryo therapy. More particularly, the present invention pertains to cryo therapy apparatuses for use in causing cold-induced apoptosis, necrosis and/or ablation.

BACKGROUND OF THE INVENTION

A number of medical conditions may be treated using ablative techniques or devices to induce cellular apoptosis. Ablative techniques, generally, result in the killing of abnormal tissue at an area of interest. Killing the abnormal tissue may result in an efficacious treatment for a medical condition. For example, atrial fibrillation may be the result of abnormal electrical activity in the left atrium and the pulmonary vein, and may be treatable by ablation of the abnormal tissue within the left atrium and/or the pulmonary vein.

Atrial fibrillation is a serious medical condition that is the result of abnormal electrical activity within the heart. This abnormal activity may occur at regions of the heart including the sino-atrial (SA) node, the atriovenricular (AV) node, the bundle of His, or within other areas of cardiac tissue. Moreover, atrial fibrillation may be caused by abnormal activity within an isolated focal center within the heart. It is believed that these foci can originate within the pulmonary vein, particularly the superior pulmonary veins.

Minimally invasive techniques have been described that use ablation catheters to target the pulmonary vein with the hope of ablating foci having abnormal electrical activity. The techniques typically are characterized by application of energy to cause lesions within the foci or other areas possessing abnormal electrical activity. Some ablation devices utilize radio frequency (RF) energy for ablation, including the device disclosed in U.S. Pat. No. 6,024,740 to Lesh et al. The RF energy devices may be used to ablate an area of interest with heat.

SUMMARY OF THE INVENTION

The present invention provides design, manufacturing, and use alternatives for devices that use cooling energy to cause cold-induced necrosis, apoptosis, and/or ablation. The present invention may comprise a cryo therapy apparatus including a core member, a cryoplasty tube coupled to the core member, and a cooling member disposed over at least a portion of the cooling tube. The cooling tube may also include a distal coil disposed about the core member. The coil may be slidable and may also be fashioned into a loop or spiral configuration.

BRIEF DESCRIPTION OF THE DRAWINGS

FIG. 2 is a cross sectional view of the cryo therapy apparatus shown in FIG. 1;

FIG. 2A is a cross sectional view of another example cyro therapy apparatus;

FIG. 3 is a cross sectional view of the cryo therapy coil;

FIG. 4 is a perspective view of the cryo therapy coil;

FIG. 5 is a side view of the cryo therapy coil;

FIG. 6 is a cross sectional view of an alternate cryo therapy apparatus;

DETAILED DESCRIPTION OF THE PREFERRED EMBODIMENTS

Figure 1:
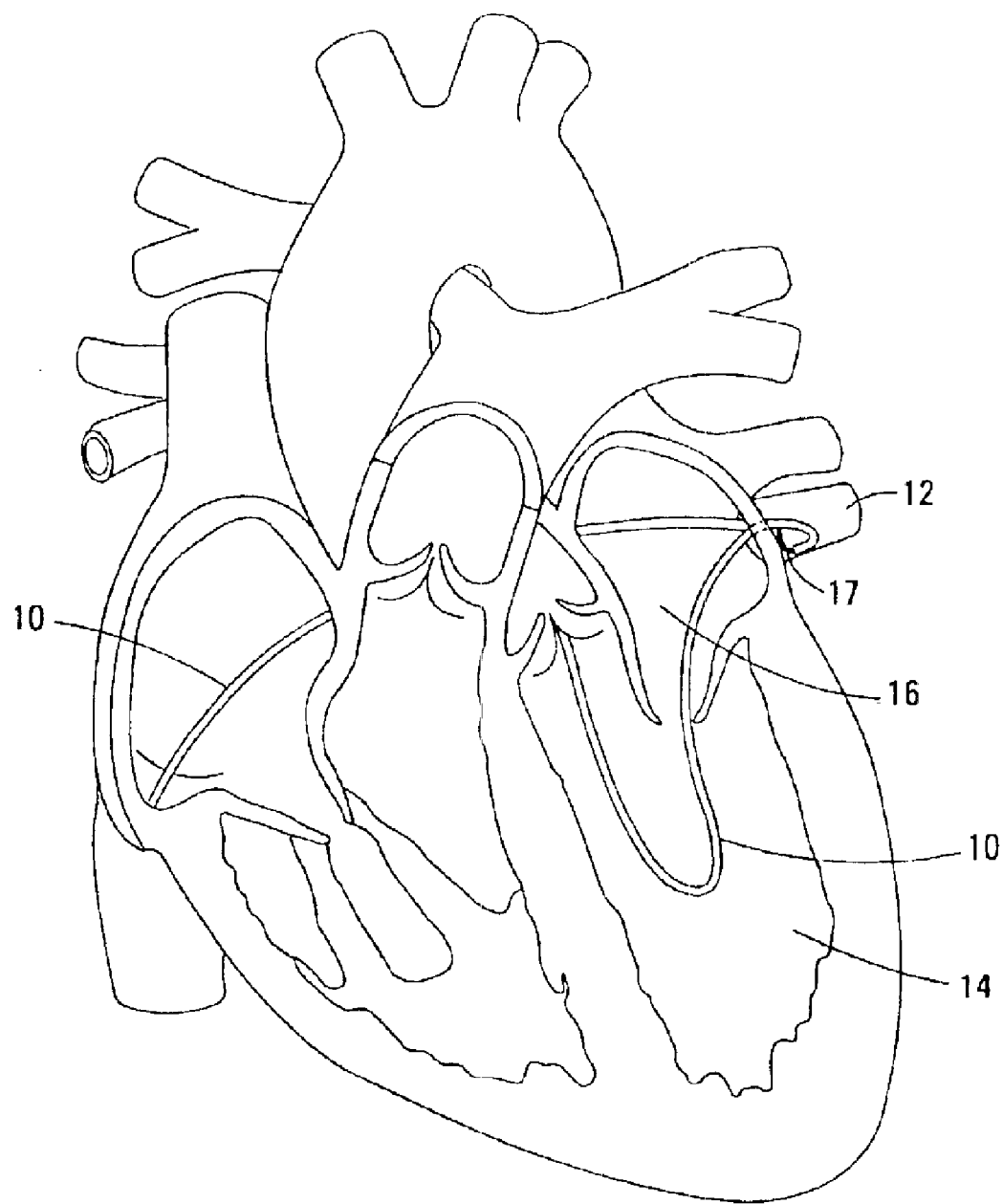
FIG. 1 is a perspective view of a cryo therapy apparatus disposed within the pulmonary vein.

The following description should be read with reference to the drawings wherein like reference numerals indicate like elements throughout the several views. The detailed description and drawings illustrate example embodiments of the claimed invention.

FIG. 1 is a perspective view of a cryo therapy apparatus 10 disposed within the pulmonary vein 12. It is believed that one potential cause of atrial fibrillation may include abnormal electrical activity within an isolated focal center within pulmonary vein 12. Atrial fibrillation may, thus, be treatable by ablating abnormal tissue within pulmonary vein 12. Cryo therapy apparatus 10 may be used to cause cold-induced necrosis and/or ablate a portion of pulmonary vein 12 or tissue proximate thereto and may constitute an efficacious treatment for atrial fibrillation.

When performing pulmonary vein ablation, cryo therapy apparatus 10 may be maneuvered through the vasculature of a patient, through the left ventricle 14, into the left atrium 16, and proximate pulmonary vein 12. Alternatively, cryo therapy apparatus 10 may also be navigated to pulmonary vein 12 via a trans-septal approach as shown in FIG. 1 and indicated by T-S. Cryo therapy apparatus 10 may be formed into a loop configuration to increase surface contact between cryo therapy apparatus 10 and pulmonary vein 12. The use of the loop configuration and increasing surface contact may make it possible for a clinician to ablate the desired portion of pulmonary vein 16. Cryo therapy apparatus 10 may then be used to cause cold-induced necrosis and/or ablation of pulmonary vein 12. Cryo therapy apparatus 10 may be manipulated into a loop configuration, for example, by actuation of a pull cord 17. Pull cord 17 may be located on the outside of cryo therapy apparatus 10 or may be disposed within cryo therapy apparatus as described below and depicted in FIGS. 7–9.

In addition to its potential utility in treating atrial fibrillation by ablating a portion of pulmonary vein 12, cryo therapy apparatus 10 may be used to treat a number of other medical conditions. For example, cryo therapy and/or cryoplasty may be efficacious in varicose vein treatment of incompetent valves, valvular disease, arrhythmia, mitral valve regurgitation therapy, gastric reflux disease, gastro esophageal reflux disease, GURD, esophageal disease, restenosis, cancer treatment including stomach or uterine cancer, etc.

FIG. 2 is a cross sectional view of cryo therapy apparatus 10. Cryo therapy apparatus 10 may include an inner tubular sheath 18, a cooling tube 20 disposed adjacent to tubular sheath 18, an outer tube 22 disposed over at least a portion of cooling tube 20, and a cooling member 24 disposed over at least a portion of cooling tube 20. Moreover, cooling tube 20 may include a distal region 26 including a coil 28 disposed about tubular sheath 18.

Tubular sheath 18 may comprise a metallic (e.g., stainless steel, nickel-titanium alloy) hypotube having a proximal end 30, a distal end 32, and a lumen 34 extending therethrough. Tubular sheath 18 (also suitably described as a core member) may be configured and adapted to be slidably disposed over a core wire 36. According to this embodiment, tubular sheath 18 may be shifted in position relative to core wire 36. This may be useful for altering the site of cold-induced necrosis and/or ablation while allowing core wire 36 to remain stationary. Core wire 36 may comprise a guidewire, tube, or other suitable structure.

Coil 28 may be slidably disposed about tubular sheath 18. In some embodiments, coil 28 is slidable disposed along essentially the entire length of sheath 18. In other embodiments, coil 28 is slidable along a portion of the length of sheath 18 (e.g., along all or a portion of the length of cooling member 24. Cooling tube 20 may also include, in addition to distal coil 28, a proximal region 38 that may be generally straight and follow the longitudinal axis of tubular sheath 18. Proximal region 38 may terminate at a proximal end (not shown) that may be coupled to a manifold, for example by a luer fitting. The manifold may comprise a coolant source and may be capable of delivering an appropriate quantity of coolant to cooling tube 20.

A portion of coil 28 may be comprised of radiopaque materials. A radiopaque material is understood to be capable of producing a relatively bright image on a fluoroscopy screen or another imaging technique during a medical procedure. This relatively bright image aids the user of cryo therapy apparatus 10 in determining the location thereof. Radiopaque materials may include, but are not limited to, gold, platinum, tungsten alloy, and plastic material loaded with a radiopaque filler. Coil 28, for example, may be at least partially gold-plated. Moreover, cryo therapy apparatus 10 may further comprise additional radiopaque markers.

Outer tube 22 may be disposed over at least a portion of cooling tube 20 near proximal region 38. Outer tube 22 may be metallic, polymeric, or a composite thereof. For example, outer tube 22 may comprise polyimide. Outer tube 22 may further comprise a support member such as a braid. A person of ordinary skill in the art may be familiar with suitable materials and configurations appropriate for the manufacturing of outer tube 22.

Cooling member 24 may be disposed over at least a portion of cooling tube 20 near distal region 26. Cooling member may be coupled to outer tube 22. Alternatively, outer tube 22 may be coupled to a distal shaft 40. According to this embodiment, distal shaft 40 may, in turn, be coupled to outer tube 22. In different embodiments, cooling member 24 may have different lengths. For example, cooling member 24 may span essentially the length of tubular sheath 14 (e.g., about 100 to 300 centimeters or more). Alternatively, the length of cooling member 24 may span a portion of the length of tubular sheath 14 or be comparable in size to typical angioplasty balloons.

Cooling member 24 may comprise a LEAP II balloon. LEAP II balloons are comprised of polyether block amide (PEBA). Polyether block amide is commercially available from Atochem Polymers of Birdsboro, Pa., under the trade name PEBAX. Alternatively, cooling member 24 may comprise a stainless steel or nickel-titanium alloy braid having a heat shrunk polymeric outer layer. Regardless of what material cooling member 24 is comprised of, cooling member may be used by allowing coil 28 may spray coolant onto an inner surface 42 of cooling member 24. Cooling member 24 may then be used to cause cold-induced necrosis or ablate tissue at an area of interest.

Cryo therapy apparatus 10 may further comprise a tube 44 having a proximal end 46, a distal end 48, and a lumen 50 extending therethrough. Lumen 50 may be a lumen that may be used to drain coolant from cooling member 24 if the temperature therein drops below a predetermined point. According to this embodiment, tube 44 may further comprise a temperature sensor 52 that may be used to quantify the temperature proximate cooling member 24.

FIG. 2A is a cross sectional view of another example cryo therapy apparatus 410, that is essentially the same in form and function as apparatus 10, expect that apparatus 410 includes an outer cooling member 425, a second outer tube 423, and defines an annular lumen 476 between second outer tube 423 and outer tube 22. Outer cooling member 425 may provide apparatus with a number of desirable characteristics. For example, outer cooling member 425 may increase the strength of apparatus 10, enhance the safety of apparatus 10, alter or enhance the cooling ability of apparatus 10, etc.

In some embodiments, annular lumen 476 may be maintained under vacuum. For example, the proximal end of second outer tube 423 may be coupled to a vacuum device or manifold. Maintaining a vacuum along the length of second outer tube 423 may insulate tube 423 to minimize heat exchange along tube 423. Moreover, if a substance becomes disposed in lumen 476 (or in a space located between outer cooling member 425 and cooling member 24) that the clinician wishes to evacuate, the substance can be removed by aspiration.

FIG. 3 is a cross sectional view of coil 28. Coil 28 may include at least one opening 54. Coolant passing through cooling tube 20 may pass through opening 54 and be sprayed onto inner surface 42 of cooling member 24. Multiple embodiments of coil 28 may include differing configurations and numbers of openings. Alterations in the number of openings or configuration of opening may be made without departing from the spirit of the invention. For example, coil 28 may include 2, 4, 6, or 8 openings arranged in a generally circular arrangement such that coolant may be sprayed as a circular ring onto inner surface 42. Spacing between openings 54 may be regular (i.e., 60° separation between 6 openings 54, 45° separation between 8 openings 54, etc.) or may be irregular.

The shape of openings 54 may be configured to allow coolant to be uniformly sprayed onto inner surface 42. For example, openings 54 may be configured to have a frusto-conical shape in order to uniformly spray coolant. Alternatively, openings 54 may have a flow directing nozzle disposed therein or be configured to have a flow directing nozzle shape in order to impart uniform coolant spray.

In use, cryo therapy apparatus 10 may be advanced across a lesion or to an area of interest in a conventional manner. Coolant may then be released through openings 54 of cooling tube 20. Cooling may drop the temperature of the tissue at an area of interest to about 0° C. to −81° C. and occur over about 2 minutes or over about 1 to 5 minutes.

The coolant used may include a low freezing point liquid such as an ethanol mixture or a liquefied gas such as $N_2O$ or $CO_2$. Liquid $N_2$ can be used as a general purpose coolant and is particularly useful when freezing of cells within the lesion is desired. Freon, $N_2O$ gas, and $CO_2$ gas can also be used as coolants. Other coolants could be used such as cold saline solution, Fluisol or a mixture of saline solution and ethanol. It is anticipated that coolants such as saline solution could be used when rapid freezing of cells within a lesion is not a treatment goal. One skilled in the art would appreciate that other coolants could be used in a similar manner to achieve one or more of the treatment goals.

For the purpose of illustration, an example of how coolant may be used is described below. Liquid $N_2O$ may be sprayed from openings 54 onto inner surface 42 of cooling member. Regulated back pressure may be maintained along the path followed by the coolant in order to prevent freezing of coolant (i.e., dry ice formation if liquid $CO_2$ is used). Cryo therapy apparatus 10 may then be used to cool (i.e., freezing, causing cold-induced lesions, ablate, etc.) an area of interest, for example the pulmonary vein. During treatment, the size and depth of orifices generated at the area of interest may be measured both before and after ablation by a number of imaging techniques including intracardiac ultrasound.

Cooling may be the result of both the Joule-Thompson effect and the latent heat of vaporization. The Joule-Thompson effect is defined as the cooling effect that comes about when a highly compressed non-ideal gas expands into a region of low pressure. The latent heat of vaporization is defined as the heat that is released as the result of the phase change from a liquid to a gas. Depending on the cryogen, the latent heat of vaporization contributes to the majority of the cooling with cryo therapy apparatus 10.

Openings 54 within coil 28 may be manufactured in a number of differing manners. An example of a way to manufacture coil 28 is depicted in FIGS. 4 and 5. FIG. 4 is a perspective view of coil 28. According to this embodiment, coil 28 may include a dimple 56 formed into coil 28. Dimple 56 may facilitate the forming of opening 54. Dimple 56 may define a portion of coil 28 having a decreased thickness. For example, coil 28 may have a diameter of about 0.008 inches and the diameter proximate coil 28 may be about 0.004 inches. The aforementioned design creates a uniform spray field for large area cryogen distribution. Alternative sizes and dimensions may be used without changing the scope of the invention.

FIG. 5 is a side view of coil 28 taken through line 4—4. Opening 54 may be formed into coil 28 at dimple 56 by a number of differing methods. For example, a cobalt puncture bit may be used to drill a hole into coil 28, thus defining opening 54. Opening 54 may have a diameter or cross-sectional area D of about 0.002 inches or may have a diameter less than about 0.010 inches.

FIG. 6 is a cross sectional view of an alternate cryo therapy apparatus 110. Cryo therapy apparatus 110 may have many of the feature described for cryo therapy apparatus 10 above and may include a cooling tube 120 slidably disposed over a core member 136. Core member 136 may include a distal end 158 having a generally tapered distal tip 160 coupled thereto. Core member 136 may comprise a stainless steel or nickel-titanium alloy core wire or may, alternatively, comprise a tubular sheath (similar to tubular sheath 18) adapted to be passed over a core wire. According to the later embodiment, distal tip 160 may further comprise a channel that a guidewire may pass through.

Although coil 128 is shown to be configured co-axially relative to core member 136, it can be appreciated that coil 128 could also be configured parallel to core member 136 or otherwise disposed within cooling member 124. Other embodiments of apparatus 110 do not include core member 136. According to these embodiments, coil 128 can be described as being slidably disposed within cooling member 124.

Cooling member 124 may comprise a polymeric heat shrink outer tube 162 disposed over a support member 164. Support member 164 may comprise a stainless steel or nickel-titanium alloy braid. Similar to what is described above, coolant may be sprayed onto inner surface 142 of cooling member 124 such that cooling member may be used for cold-induced necrosis and/or ablation of tissue. In addition to being coupled to core member 136, distal tip 160 may also be coupled to support member 164, for example by soldering. Outer tube 120 may be coupled to cooling member 124.

Similar to what is disclosed above, cooling tube 120 may include a coil 128 disposed proximate distal end 158 of core member 136. Coil 128 may include at least one opening 154 adapted to spray coolant onto an inner surface 142 of cooling member 124. Coil 128 may be slidable along the length of core member 136. This feature may allow heat exchange to occur at a number of points along the length of cooling member 124.

Cryo therapy apparatus 110 may also include tube 144 that may be similar to that described above. Alternatively, tube 144 may be coupled directly to cooling tube 120. According to this embodiment, tube 144 would be slidable relative to core member 156. More particularly, tube 144 may be coupled to cooling tube 120 such that movement of cooling tube 120 relative to core member 156 may result in substantially similar movement of tube 144.

Figure 7:
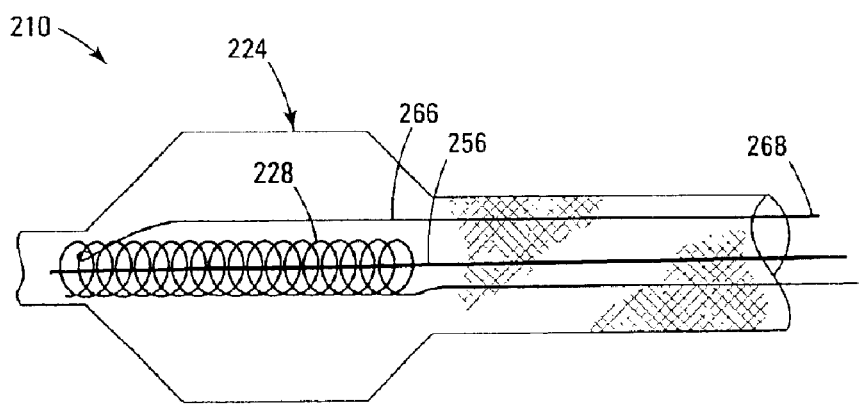
FIG. 7 is a cross sectional view of a cryo therapy apparatus having a pull cord.

It may be desirable to precisely control the position of a cryo therapy apparatus (including those described herein) when performing a medical procedure. FIG. 7 is a cross sectional view of a cryo therapy apparatus 210 device having a pull cord 266. It should be noted that the use of pull cord 266 may be applicable to other embodiments of a cryo therapy apparatus including those described herein. Pull cord 266 may have a proximal end that is directly or indirectly accessible to the clinician and a distal end 268. Distal end 268 may be coupled to any one of a number of locations along the length of cryo therapy apparatus 210. For example, distal end 268 of pull cord 266 may be coupled to coil 228. Alternatively, distal end 268 may be coupled to core member 256.

Figure 8:
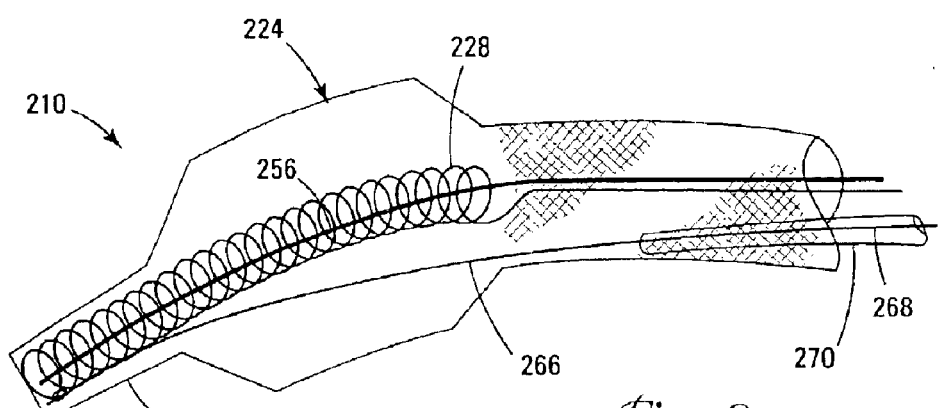
FIG. 8 is a cross sectional view of the cryo therapy apparatus shown in FIG. 7, wherein the pull cord is actuated.

FIG. 8 is a cross sectional view of cryo therapy apparatus 210 wherein pull cord 266 is actuated in order to alter the position of cryo therapy apparatus 210. Also shown in FIG. 8 is an optional sheath 270 disposed within apparatus 210 for at least a portion of pull cord 266 to pass through. By actuating pull cord 266, cryo therapy apparatus 210 may be bent or otherwise altered into a number of differing shapes and configurations. A person of ordinary skill in the art may be familiar with different configurations appropriate for multiple embodiments of the invention.

It can also be seen in FIG. 8 that coil 228 may be slidable along core member 256 (or, more generally, slidable within cooling chamber 224) and can be slid toward the distal end of cooling chamber 224. In some embodiments, coil 228 can be advanced to a necked distal region 272 disposed at the distal end of cooling chamber 224. This may aid deflection of apparatus 210 when pull cord 266 is actuated. More particularly, advancing coil 256 to a position adjacent necked distal region 272 may allow a clinician to deflect the distal end of apparatus 210 as appropriate.

Figure 9:
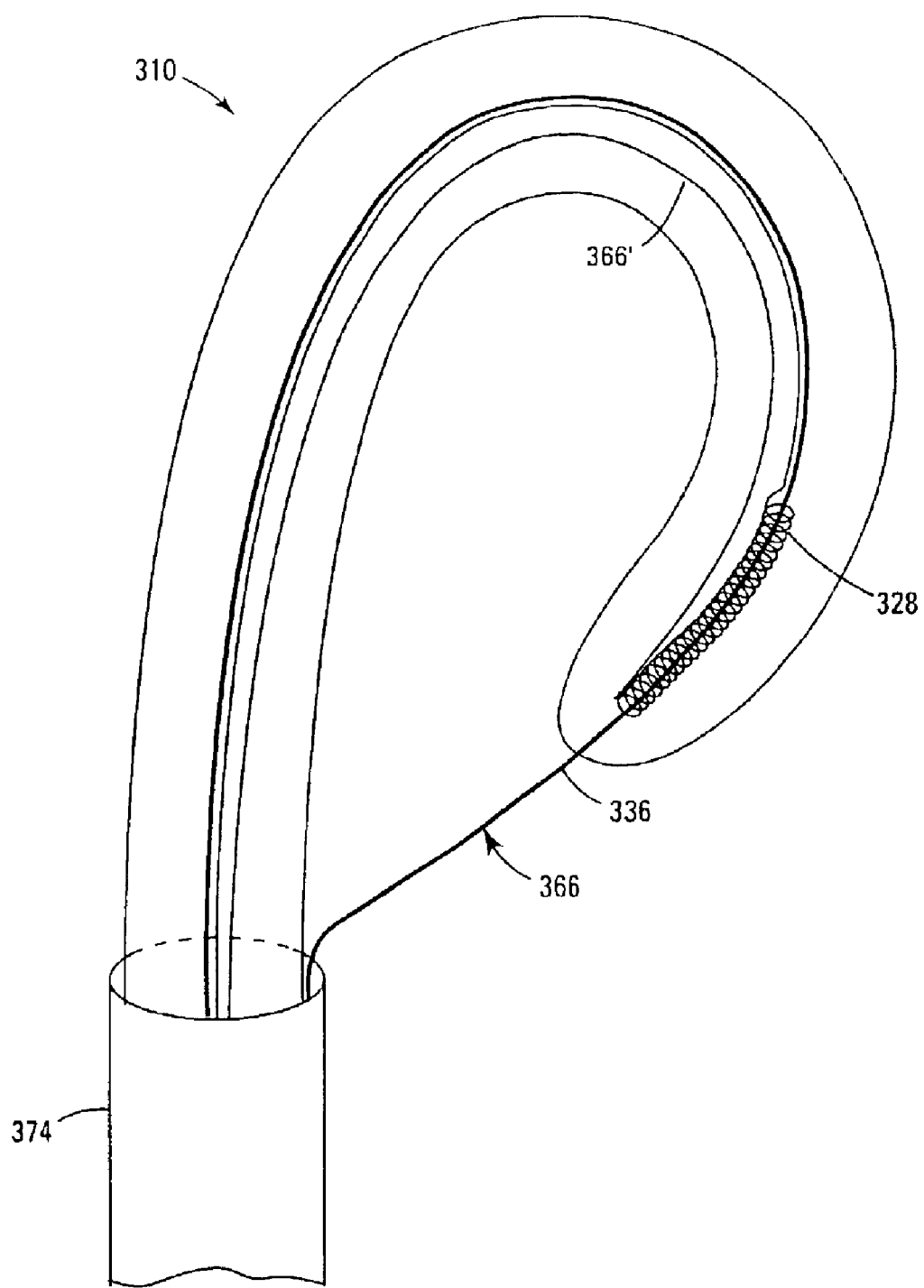
FIG. 9 is a perspective view of a slidable cryo coil in a loop configuration.

As an alternate to what is shown in FIG. 8, a portion of pull cord 266 may be located outside or extend out of the distal end of cryo therapy apparatus 210. For example, FIG. 9 illustrates cryo therapy apparatus 310 in a loop configuration with pull cord 366 extending out of the distal end of apparatus 310. Apparatus 310 is essentially the same in form and function as other cryo therapy apparatuses described herein and may include a catheter sheath 374 disposed over at least a portion thereof. Pull cord 366 (which may or may not be directly coupled to coil 328) can extend out of the distal end of apparatus 310, loop back into sheath 374, and then extend back in the proximal direction where it would be accessible to a clinician. This configuration may improve the ability of the clinician to control and manipulate a loop configuration of apparatus 310. In some embodiments, pull cord 366 may comprise an elongate shaft or guidewire 336. In other embodiments, apparatus 310 may also include a second pull cord (indicated by reference number 366') that can be used in a manner essentially the same as pull cord 266 of FIGS. 7 and 8.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A cryo therapy apparatus, comprising:
    an elongate core member adapted to be slidably disposed about a core wire;
    a cryo tube disposed adjacent to the core member, the cryo tube having a proximal region and a distal region;
    wherein the distal region includes a coil disposed about at least a portion of the core member, the coil including at least one opening;
    an outer tube disposed over at least a portion of the cryo tube; and
    a cooling member disposed over the coil and coupled to the outer tube.

2. The cryo therapy apparatus in accordance with claim 1, further comprising the core wire about which the core member is slidably disposed.

3. The cryo therapy apparatus in accordance with claim 1, wherein at least a portion of the coil comprises gold.

4. The cryo therapy apparatus in accordance with claim 1, wherein the coil includes one or more openings.

5. The cryo therapy apparatus in accordance with claim 4, where the openings are frusto-conical in shape.

6. The cryo therapy apparatus in accordance with claim 1, further comprising a tube disposed within the outer tube, the tube having a distal end disposed within the cooling member.

7. The cryo therapy apparatus in accordance with claim 6, wherein the tube further comprises a temperature sensor.

8. The cryo therapy apparatus in accordance with claim 1, wherein the outer tube includes a support member.

9. The cryo therapy apparatus in accordance with claim 8, wherein the support member includes a braid.

10. The cryo therapy apparatus in accordance with claim 1, wherein the cooling member includes a support member.

11. The cryo therapy apparatus in accordance with claim 10, wherein the support member includes a braid.

12. The cryo therapy apparatus in accordance with claim 1, wherein the cooling member comprises a balloon.

13. The cryo therapy apparatus in accordance with claim 1, further comprising an outer member disposed over the cooling member.

14. The cryo therapy apparatus in accordance with claim 13, further comprising a second outer tube disposed over the outer tube, and wherein the outer member is coupled to the second outer tube.

15. The cryo therapy apparatus in accordance with claim 1, further comprising a pull wire having a proximal and a distal end, wherein at least a portion of the proximal end is disposed within the outer tube and wherein the distal end is coupled proximate to a distal end of the coil.

16. A cryo therapy apparatus, comprising:
    an elongate core wire having a proximal end and a distal end;
    a tubular sheath disposed about and slidable along the core wire;
    a cryo tube disposed adjacent to the tubular sheath, the cryo tube having a proximal end and a distal end;
    wherein the distal end includes a coil disposed about at least a portion of the tubular sheath, the coil including one or more openings;
    an outer tube disposed over at least a portion of the cryo tube;
    a cooling member disposed over the coil and coupled to the outer tube; and
    a tube disposed within the outer tube, the tube having a distal end disposed within the cooling member.

17. The cryo therapy apparatus in accordance with claim 16, wherein at least a portion of the coil comprises gold.

18. The cryo therapy apparatus in accordance with claim 16, wherein the openings have the shape of a flow directing nozzle.

19. The cryo therapy apparatus in accordance with claim 16, wherein the tube further comprises a temperature sensor.

20. The cryo therapy apparatus in accordance with claim 16, wherein the outer tube includes a support member.

21. The cryo therapy apparatus sin accordance with claim 20, wherein the support member includes a braid.

22. The cryo therapy apparatus sin accordance with claim 16, wherein the cooling member includes a support member.

23. The cryo therapy apparatus in accordance with claim 22, wherein the support member includes a braid.

24. The cryo therapy apparatus in accordance with claim 16, wherein the cooling member comprises a balloon.

25. The cryo therapy apparatus in accordance with claim 16, further comprising an outer cooling member disposed over the cooling member.

26. The cryo therapy apparatus in accordance with claim 25, further comprising a second outer tube disposed over the outer tube, and wherein the outer cooling member is coupled to the second outer tube.

27. The cryo therapy apparatus in accordance with claim 16, further comprising a pull wire having a proximal and a distal end, wherein at least a portion of the proximal end is disposed within the outer tube and wherein the distal end is coupled proximate to a distal end of the coil.

28. A method of causing cold-induced necrosis or apoptosis, comprising the steps of:
    advancing across a target site a cryo therapy apparatus including an elongate core wire having a proximal end and a distal end; a tubular sheath disposed about and slidable upon the core wire; a cryo tube coupled to the tubular sheath, the cryo tube having a proximal end and a distal end; wherein the distal end includes a coil disposed about at least a portion of the tubular sheath, the coil including at least one opening; an outer tube disposed over at least a portion of the cryo tube; and a cooling member disposed over the coil and coupled to the outer tube;
    delivering coolant through the cryo tube, wherein coolant passes through openings within the coil and is sprayed onto an interior surface of the cooling member; and
    cooling cells within the target site.

29. The method in accordance with claim 28, wherein the target site is a chamber of the heart.

30. The method in accordance with claim 28, wherein the target site is an artery.

31. The method in accordance with claim 28, wherein the target site is a vein.

32. The method in accordance with claim 28, wherein the target site is the esophagus.

33. The method in accordance with claim 28, wherein the target site is the trachea.

34. The method in accordance with claim 28, wherein the target site is an intestine.

35. The method in accordance with claim 28, wherein the cryo therapy apparatus further comprises a pull wire having a proximal and a distal end, wherein at least a portion of the proximal end is disposed within the outer tube and wherein the distal end is coupled proximate to a distal end of the coil.

36. The method in accordance with claim 35, further comprising the step of deflecting the cryo therapy apparatus by pulling on the pull wire.

37. The method in accordance with claim 28, wherein the cryo therapy apparatus further comprises a tube disposed within the outer tube, the tube having a distal end disposed within the cooling member.

38. The method in accordance with claim 37, further comprising the step of draining coolant from the cooling member through the tube.

39. A cryo therapy apparatus, comprising:
- a core wire;
- an elongate core member comprising a tubular sheath adapted to be slidably disposed about the core wire; and
- a cryo tube disposed adjacent to the core member, the cryo tube having a proximal region and a distal region, wherein the distal region includes a coil disposed about at least a portion of the core member, the coil including at least one opening, an outer tube disposed over at least a portion of the cryo tube, and a cooling member disposed over the coil and coupled to the outer tube.

* * * * *

UNITED STATES PATENT AND TRADEMARK OFFICE
CERTIFICATE OF CORRECTION

PATENT NO. : 6,929,639 B2
DATED : August 16, 2005
INVENTOR(S) : Daniel M. Lafontaine It is certified that error appears in the above-identified patent and that said Letters Patent is hereby corrected as shown below:

Column 7,
Line 61, after "proximal" insert -- end --;

Column 8,
Lines 23 and 25, delete "sin" and insert -- in --;
Line 39, after "proximal" insert -- end --;

Column 9,
Line 7, after "proximal" insert -- end --.

Signed and Sealed this

Sixteenth Day of May, 2006

JON W. DUDAS
*Director of the United States Patent and Trademark Office*